Figure 1:
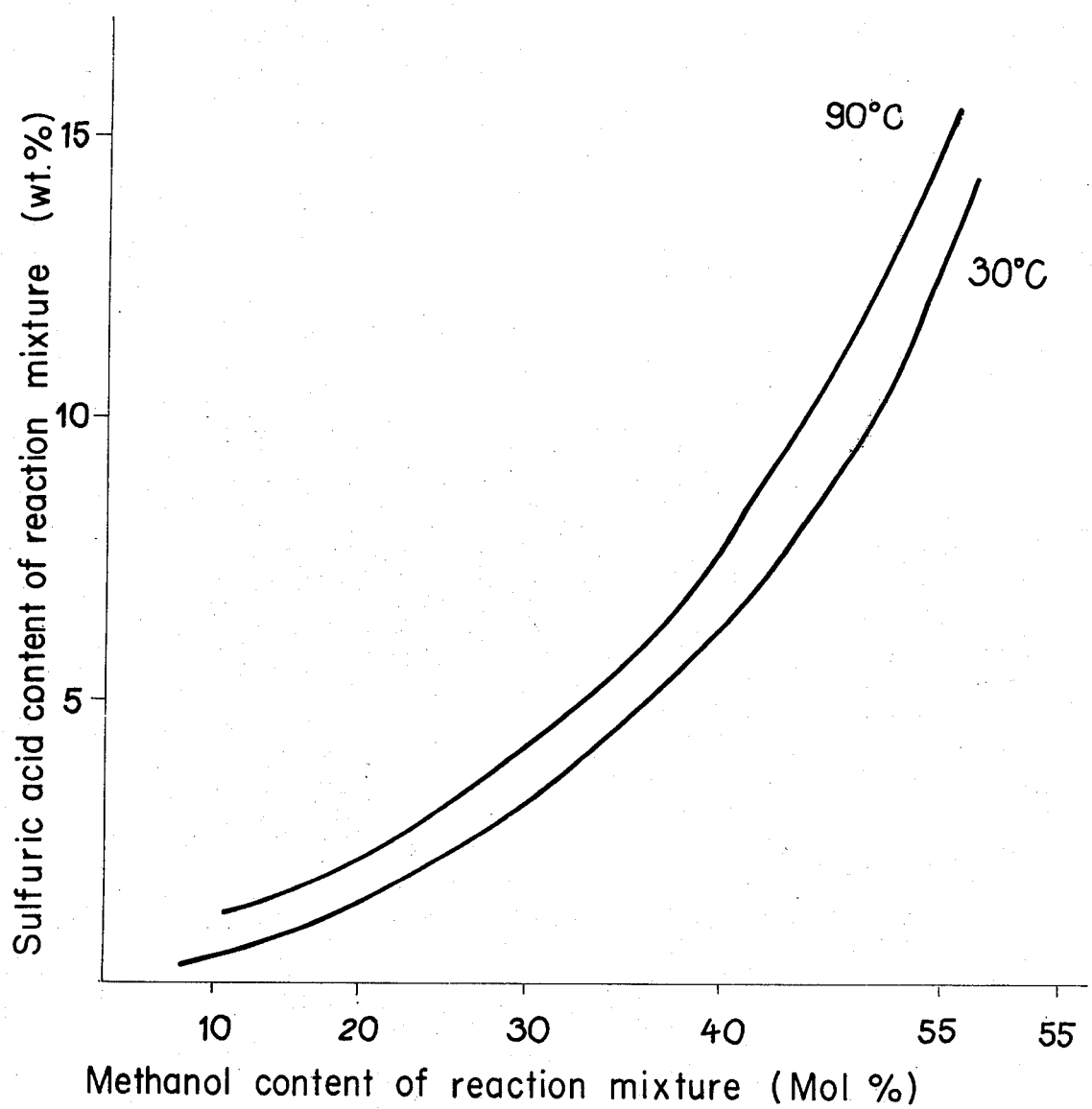

United States Patent [19]

Laky et al.

[11] 4,242,526
[45] Dec. 30, 1980

[54] PROCESS FOR THE DIRECT SEPARATION OF ISOBUTYLENE FROM MIXTURES OF HYDROCARBONS

[75] Inventors: János Laky; Rezső Csikös, both of Veszprém; Lajos Péterfy, Balatonkenese; Lajos Szvetelszky, Répcelak; István Pallay, Budapest, all of Hungary

[73] Assignee: Magyar Ásványolaj és Földgáz Kisérleti Intézet, Veszprém, Hungary

[21] Appl. No.: 884,607

[22] Filed: Mar. 8, 1978

Related U.S. Application Data

[63] Continuation of Ser. No. 729,784, Oct. 5, 1976, abandoned.

[51] Int. Cl.$^2$ .................. C07C 41/06; C07C 41/10
[52] U.S. Cl. .................................. 568/697; 568/699
[58] Field of Search ............. 260/614 A; 568/697, 568/699

[56] References Cited

U.S. PATENT DOCUMENTS

| | | | |
|---|---|---|---|
| 1,968,601 | 7/1934 | Edlund et al. | 260/614 A |
| 2,067,385 | 1/1937 | Evans et al. | 260/614 A |
| 2,139,359 | 12/1938 | Evans et al. | 260/614 A |
| 2,391,084 | 12/1945 | Carmody | 260/614 A |
| 2,721,222 | 10/1955 | Cottle et al. | 260/614 A X |
| 3,121,124 | 2/1964 | Verdol | 260/614 A |
| 3,846,088 | 11/1974 | Brown et al. | 260/614 A |

OTHER PUBLICATIONS

Evans et al. II, I/EC, 28, No. 10, 1186–1188, 1936.

Primary Examiner—Howard T. Mars

[57] ABSTRACT

Methyl tertiary butyl ether is produced from a mixture of $C_4$ hydrocarbons containing isobutylene and butadiene. The isobutylene is selectively reacted with a greater than stoichiometric amount of methanol at a temperature of 50 to 120 degrees C., in a homogeneous liquid phase and in the presence of a catalytic amount of sulfuric acid. The sulfuric acid is present in an amount less than 20% by weight based on the weight of the reaction mixture. The homogeneous liquid phase is maintained throughout the reaction whereby a reaction mixture containing methyl tertiary butyl ether is produced and undesired polymerization of the badadiene is avoided. The reaction mixture is cooled then reaction mixture which has been washed free of methanol, or separated unreacted $C_4$ fraction which is isobutylene-free, is added. An upper phase containing hydrocarbons and methyl tertiary butyl ether and a part of the methanol and a lower phase containing methanol and 10 to 50% sulfuric acid is formed. The lower phase is recirculated as a catalyst to the step of selectively reacting the isobutylene with methanol.

1 Claim, 3 Drawing Figures

PROCESS FOR THE DIRECT SEPARATION OF ISOBUTYLENE FROM MIXTURES OF HYDROCARBONS

This is a continuation of application Ser. No. 729,784, filed on Oct. 5, 1976, now abandoned.

The invention relates to a process for the direct obtaining of isobutylene. The process is equally suitable for the removal of isobutylene from gas mixtures having a high butadiene content or from gas mixtures containing only butenes and butane, by means of selective reaction with methanol. The formed methyl tert.butyl ether (NTBE) can be easily separated from the $C_4$ hydrocarbons. Most parts of the isobutylene used in the art originate from the $C_4$ fraction obtained via pyrolysis or out of butane-de-hydrogenation processes. However, these processes do not yield pure isobutylene and the product contains also other olefins and diolefins in addition to saturated hydrocarbons. A more purified compound can be obtained only by using expensive equipments and complicated operations.

The $C_4$ fraction arising from the pyrolysis of hydrocarbons and gas mixtures prepared by dehydrogenation processes could not serve hitherto as direct sources of isobutylene, due to their high butadiene contents. In the known processes at first butadiene is extracted and after isobutylene is separated generally by means of absorption with sulphuric acid (G. D. Hobson: Modern Petroleum Techn. p. 460). Tert. butanol is formed in the course of the absorption which after purification is dehydrated and yields pure isobutylene.

Isobutylene can be reacted also with methanol in the presence of acidic catalysts when MTBE is formed. According to the British Patent specification No. 1,165,479 e.g. MTBE can be easily decomposed over an $Al_2O_3$ catalyst to methanol and pure isobutylene. A further advantage is that the formed MTBE may be used preferably as a component having high octane number in motor gasolines.

A requirement of environmental protection is to reduce the lead content of gasolines. This requires in turn a possibly cheap method for the production of gasoline components having high octane number. In this field the production of MTBE from isobutene-containing gas mixtures represents a significant technical progress.

The reaction of isobutene with methanol in the presence of acidic catalysts has been described by T. E. Evans (Ind. Eng. Chem. 28 /N 10/ 1186). Sulphuric acid is the most efficient catalyst of this reaction. In the process according to the U.S. Pat. No. 2,721,222 (Esso Res. Eng. Co.) similarly sulphuric acid is used as catalyst. The reaction is carried out in a heterogeneous phase, then the reaction mixture is diluted with a great amount of methanol in order to decrease the decomposition during distillation. According to the U.S. Pat. No. 2,720,547 (Standard Oil Co.) the reaction is carried out similarly in a heterogeneous phase and 80% sulphuric acid or alkane-sulphonic acid is applied as catalyst in order to decrease decomposition during distillation as a consequence of using a catalyst of lower activity. However, up to the present it was not possible to solve by means of a simple method the problem of the separation and recirculation of the catalyst. Thus, the recently applied processes are using in general solid heterogeneous catalysts. In the majority of processes one operates with an ion exchanger catalyst of a sulphonated type of styrene-divinylbenzene base. Processes of this type are e.g. those described in the Belgian Pat. No. 612,338 (Bayer), in the U.S. Pat. No. 3,170,000 (Sinclair Res. Inc.) or in the British Pat. No. 1,176,620 (Shell). However, these catalysts have essentially lower activities and are extremely sensitive to even small contaminations of the raw materials. In general, these processes lend themselves only to the conversion of pure isobutylene because in this case the low conversion can be increased by recirculating the butane and the amount of detrimental contaminants such as butadiene is small. The processing of mixtures of isobutylene and n-butylene is limited because of the low conversion. According to the latest processes, German Pat. No. 2,246,004 (Sun Oil Co.) only a part of isobutylene is allowed to react and the gas mixture with the residual isobutylene content is then used for other purposes.

The prerequisite of the economic production of MTBE out of isobutylene and methanol is the possibility of producing MTBE by the direct extraction of the isobutylene content of gases of various origin. For this purpose the best suitable raw material is the $C_4$ fraction of the gasoline pyrolysis. However, the isobutylene content of the mixture of $C_4$ hydrocarbons which contains about 40% of butadiene could not be obtained economically by known processes. Namely, butadiene polymerizes readily under the action of strong acids and reacts also with methanol. This is shown in the U.S. Pat. No. 2,922,822 (Esso Res. Eng. Co.) according to which unsaturated ethers are proced from butadiene-containing gases and from methanol under conditions similar to those of the reaction of isobutylene.

In the course of our experimental work we examined thoroughly the behaviour of butadiene under the conditions under which MTBE is being produced. It was found in these experiments that isobutylene can be selectively reacted in the presence of butadiene provided the amount of sulphuric acid applied as catalyst is below 20% by weight calculated on the reaction mixture and the reaction is carried out at a temperature between 50° and 120° C. in a homogeneous liquid phase with an excess of methanol. Under such conditions the polymerization of butadiene can be reduced to a neglibible extent.

The methanol addition of isobutylene takes place under these conditions in a thousand times higher rate than the reaction rate of butadiene and methanol. According to the process of invention isobutylene reacts completely selectively with methanol even in the case if the raw material contains 40 to 60% of butadiene.

The environmental protection necessitates the decrease of the amount of sulphuric acid involved in the process. This can be accomplished in the present invention by a recirculation of the catalyst. Investigations were carried out to establish the dissolving capacity of the reaction mixture having a different composition relating to sulphuric acid. It has been recognized that under particular conditions after a reaction carried out at a temperature between 50° and 120° C. in a homogeneous liquid phase, the reaction mixture when cooled to room temperature, a major part of the catalyst forms a separate phase with a part of the excess methanol. The separated lower phase contains 10 to 50% of sulphuric acid and can be directly employed as a catalyst of the synthesis. The separation of this catalyst phase after the reaction is influenced by the proportion of methanol to isobutylene and by the sulphuric acid content. In FIG. 1 the values of the maximum concentration of sulphuric acid in per cent by weight are plotted against the contents of methanol at 90° C. and 30° C. These data relate to a raw material having 95% of isobutylene content. In the case of an identical methanol content the amount of dissolved sulphuric acid decreased parallely to the decrease of the isobutene content whereas the amount of dissolved sulphuric acid increases with the increase of the molar ratio of methanol, as shown by FIG. 1. The deviation between the two curves shows the separating efficiency of the catalyst which takes place on the effect of cooling. The initial molar ratio of methanol to isobutylene is apparently reduced by the amount of methanol entering the sulphuric acid phase, increasing in this way the amount of separated sulphuric acid.

Figure 2:
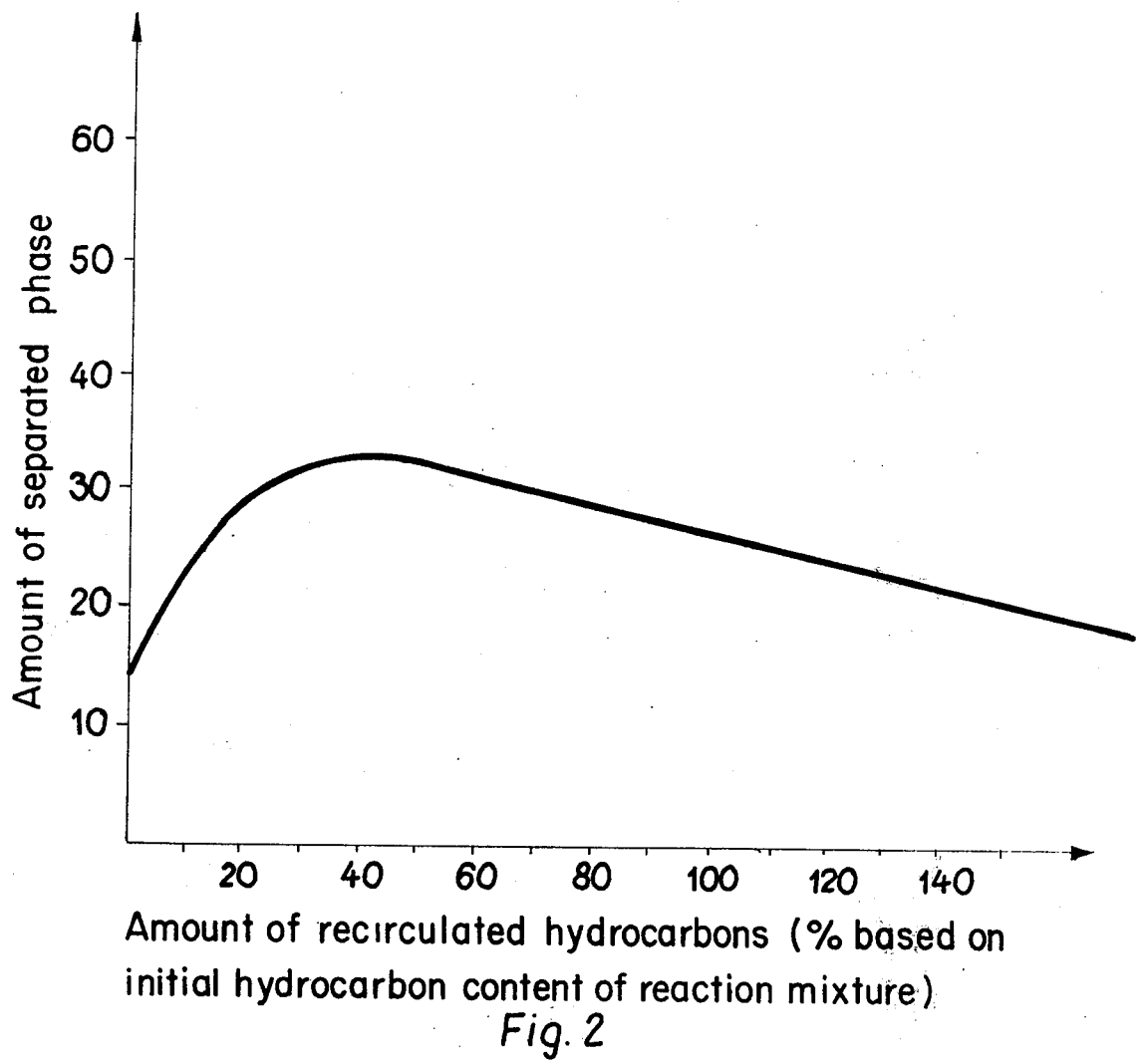

It has been found that the separation of the catalyst can be promoted by recirculating after, the reaction mixture free of methanol or the $C_4$ fraction set free from isobutylene which fraction leaves the process. The surprising efficiency of recirculating is illustrated by FIG. 2 which shows the amount of the separated phases plotted against the amount of hydrocarbons recirculated. The amount of hydrocarbons which have been recirculated are given in per cent referred to the initial hydrocarbon content of the reaction mixture. The curve on FIG. 2 relates to the product of the reaction of a hydrocarbon mixture having 27% of isobutylene content, carried out at a 3.5 molar ratio of methanol to isobutylene and in the presence of 3.2% by weight of sulphuric acid as catalyst up to a 90% converseion of isobutylene. As conversion by the curve on FIG. 2, the amount of the separated phase is remarkably influenced by already small amounts of recirculated material whereas the recirculation of greater amounts of material did not influence significantly the amount of separated phase.

The two effects referred to namely the decrease of temperature and the decrease of methanol content make possible either alone or combined a separation of the sulphuric acid in a rather simple way. The separated phase having high sulphuric acid content can be preferably employed directly as catalyst. It is of advantage that the costs of recovering excess methanol is reduced because the recovery of methanol content of the catalyst phase can be easily carried out.

Figure 3:
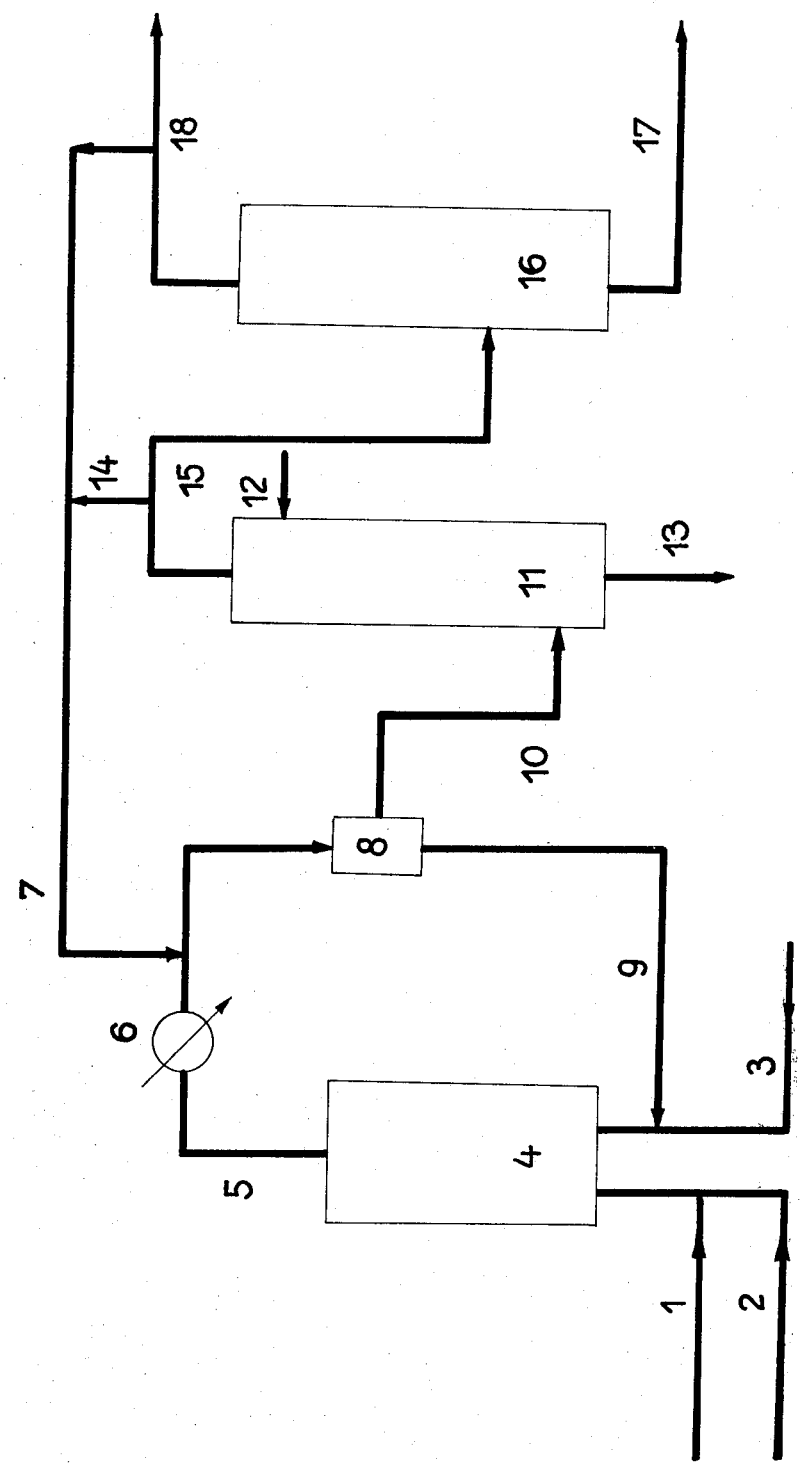

The flow scheme of the claimed process is shown on FIG. 3.

The isobutylene-containing mixture of hydrocarbons is fed through pipeline 1 and methanol through pipeline 2 into reactor 4. Fresh sulphuric acid catalyst is introduced into reactor 4 through pipeline 3 whereas the catalyst solution separated from the reaction mixture through pipeline 9. The reaction takes place in a homogeneous liquid phase. The reaction mixture leaving reactor 4 through pipeline 5 is cooled in condenser 6. Simultaneously with the cooling of the batch a part of the hydrocarbon fraction from which isobutylene has been removed and is recirculated through pipeline 7 and/or a part of the reaction mixture free from methanol is recirculated as well through pipelines 7 and 14. Under the effect of cooling and recirculating the homogeneous reaction mixture is decomposed in two phases which are subsequently separated in separator 8. The lower phase having a high sulphuric acid content and serving as catalyst is transferred from separator 8 through pipeline 9 into reactor 4. The upper phase with a decreased sulphuric acid content is conducted in turn through pipeline 10 into washing tank 11 whereto water containing if necessary alkali is fed through pipeline 12 in order to remove traces of catalyst. The washing water leaving the tank 11 through pipeline 13 contains the excess of methanol used in the reaction. This excess of methanol can be separated in a known way by distillation and then recirculated in the reaction system. The reaction mixture after having removed the methanol, leaving the system through pipeline 15 is partly recirculated through pipelines 14 and 7 to the separation of the catalyst. The residual part is transferred through pipeline 15 into distilling column 16 where the unreacted hydrocarbons are separated from MTBE. The hydrocarbon mixture after removing the isobutylene leaves the column at the top through pipeline 18. However, a part of the leaving mixture is recirculated to the separation step of the catalyst through pipeline 7. The MTBE formed from the isobutylene present originally in the raw material leaves the column at the bottom through pipeline 17. The MTBE obtained here can be used directly or eventually after an adequate purification as a component of motor fuels or can be decomposed to isobutylene and methanol.

It can be seen from the abovementioned process that it is suitable in a wider concentration range for the conversion of the isobutylene content of gaseous mixtures of hydrocarbons in to MTBE even in case of raw materials having a high butadiene content. A further advantage is that sulphuric acid can be applied in the process as a catalyst having high activity and low price and that a considerable part of the sulphuric acid can be separated after the reaction and recirculated.

The process is illustrated by the Examples given below:

EXAMPLE 1

Into a 0.5 liter autoclave lined with polypropylene 259.8 ml. of liquid isobutylene of 95% purity, 140.2 ml. of methanol and 9.5 g. of sulphuric acid are fed at −20° C. The reaction is carried out at 90° C., the reaction mixture is homogeneous and 87% of isobutylene is converted into MTBE in 20 minutes. On cooling the reaction mixture, a phase of higher specific gravity is separating from the product. This phase contains beside methanol more than 80% of the sulphuric acid catalyst introduced. On recirculating the catalyst phase and calculating the amount thereof in a concentration corresponding to its content of sulphuric acid and methanol, no difference was observed carrying out the reaction and the separability of the catalyst phase from the reaction product remained as good as in the previous step.

EXAMPLE 2

Into a reactor kept under a pressure of 20 atm and at a temperature of 90° C. continuously 5 liters/hour of a liquid $C_4$ fraction (containing 25% of isobutane and 41% of butadiene) originating from gasoline pyrolisis, 1.22 liter of methanol, 15 ml. of sulphuric acid and 0.75 liter of catalyst solution containing sulphuric acid are introduced. The isobutylene content of the raw material in the homogeneous reaction mixture leaving the reactor is converted in a rate of 93.8% into MTBE. The reaction mixture is cooled and at the same time 1 liter/hour of $C_4$ fraction free from isobutylene added. The catalyst solution containing 26.9% of sulphuric acid which is separating from the reaction mixture owing to its higher specific gravity is recirculated to the entry of the reactor whereas the upper phase is introduced into an aqueous washing vessel kept under pressure of 5 atm in order to remove excess methanol. The washing water contained 2% of sodium hydroxide which serves for the removal of traces of the catalyst. The reaction mixture after removal of methanol is decomposed in an apparatus for continuous distillation to MTBE and to fractions containing $C_4$ hydrocarbons under a pressure of about 4 atm. A part of these $C_4$ hydrocarbons is recirculated to the separation step of the catalyst. The capacity of the apparatus of the amount to 3.8 liter/hour of liquid $C_4$ hydrocarbons having 2% of isobutylene and 52% of butadiene content.

EXAMPLE 3

Into the reactor described in Example 2, continuously 5.0 liters/hour of a liquid $C_4$ fraction containing 20% of isobutene which fraction originates from catalytic cracking, 1.0 liter of methanol, 10 ml. of 98% sulphuric acid and 0.65 liter of catalyst solution are introduced. To the reaction mixture leaving the reactor 1.2 liter/hour of reaction mixture already free from methanol is recirculated and at the same time the reaction mixture is cooled to room temperature. The separated catalyst phase contains 25.4% of sulphuric acid. Then methanol is removed from the reaction mixture by washing it with water and a part of the reaction mixture containing MTBE and $C_4$ hydrocarbons is recirculated for the separation of the catalyst. The residual part is fed into a distilling apparatus where the residual $C_4$ hydrocarbons are separated from MTBE. 94.6% of the introduced isobutylene was converted. The $C_4$ gas leaving the system contained more than 98% of the introduced n-butylenes.

What we claim is:

1. A process for producing methyl tertiary butyl ether from a mixture of $C_4$ hydrocarbons containing isobutylene and butadiene, comprising the steps of selectively reacting the isobutylene with a greater than stoichiometric amount of methanol, at a temperature of 50 to 120 degrees C., in a homogeneous liquid phase and in the presence of a catalytic amount of sulfuric acid, said sulfuric acid being present in an amount less than 20% by weight based on the weight of the reaction mixture, said homogeneous liquid phase being maintained throughout the reaction, whereby a reaction mixture containing methyl tertiary butyl ether is produced and undesired polymerization of the budadiene is avoided; cooling the reaction mixture then adding to it reaction mixture which has been washed free of methanol or separated unreacted $C_4$ fraction which is isobutylene-free whereby an upper phase containing hydrocarbons and methyl tertiary butyl ether and a part of the methanol and a lower phase containing methanol and 10 to 50% sulfuric acid is formed; and recirculating the lower phase as a catalyst to said step of selectively reacting the isobutylene with methanol.

* * * * *